(12) United States Patent
Clark et al.

(10) Patent No.: US 9,233,099 B2
(45) Date of Patent: Jan. 12, 2016

(54) METHODS OF TREATING COGNITIVE DYSFUNCTION BY MODULATING BRAIN ENERGY METABOLISM

(71) Applicants: Joseph F. Clark, Cincinnati, OH (US); Antonius J. de Grauw, Cincinnati, OH (US)

(72) Inventors: Joseph F. Clark, Cincinnati, OH (US); Antonius J. de Grauw, Cincinnati, OH (US)

(73) Assignees: University of Cincinnati, Cincinnati, OH (US); Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 14/266,258

(22) Filed: Apr. 30, 2014

(65) Prior Publication Data

US 2014/0235687 A1 Aug. 21, 2014

Related U.S. Application Data

(63) Continuation-in-part of application No. 13/347,867, filed on Jan. 11, 2012, now abandoned.

(51) Int. Cl.
*A61K 31/415* (2006.01)
*A61K 31/4168* (2006.01)

(52) U.S. Cl.
CPC .................................. *A61K 31/4168* (2013.01)

(58) Field of Classification Search
CPC .................................................. A61K 31/4168
USPC ............................................................ 514/401
See application file for complete search history.

(56) References Cited

U.S. PATENT DOCUMENTS

| | | | |
|---|---|---|---|
| 4,788,179 A | 11/1988 | Flohe et al. |
| 4,981,774 A | 1/1991 | Tai et al. |
| 5,091,404 A | 2/1992 | Elgebaly |
| 5,321,030 A | 6/1994 | Kaddurah-Daouk et al. |
| 5,324,731 A | 6/1994 | Kaddurah-Daouk et al. |
| 5,492,930 A | 2/1996 | Coffin |
| 5,676,978 A | 10/1997 | Teicher et al. |
| 5,741,661 A | 4/1998 | Goldin et al. |
| 5,837,737 A | 11/1998 | Goldin et al. |
| 5,866,537 A | 2/1999 | Bianchi |
| 5,886,040 A | 3/1999 | Fang |
| 5,998,457 A | 12/1999 | Kaddurah-Daouk |
| 6,075,031 A | 6/2000 | Kaddurah-Daouk et al. |
| 6,166,249 A | 12/2000 | Pischel et al. |
| 6,169,115 B1 | 1/2001 | Kaddurah-Daouk |
| 6,193,973 B1 | 2/2001 | Tuttle |
| 6,242,491 B1 | 6/2001 | Kaddurah-Daouk |

(Continued)

FOREIGN PATENT DOCUMENTS

| | | |
|---|---|---|
| DE | 19830768 | 1/2000 |
| DE | 19929994 | 1/2000 |

(Continued)

OTHER PUBLICATIONS

Rosenberg et al. 'High prevalence of SLC6A8 deficiency in X-linked mental retardation,' Am. J. Hum. Genet. 2004, vol. 75, pp. 97-105.*

(Continued)

*Primary Examiner* — Shengjun Wang
(74) *Attorney, Agent, or Firm* — Dinsmore & Shohl LLP (57) ABSTRACT

Methods for treating cognitive dysfunction by modulating brain energy metabolizm using cyclocreatine or a pharmaceutically acceptable salt thereof are discussed.

13 Claims, 7 Drawing Sheets

(56) References Cited

U.S. PATENT DOCUMENTS

| | | | |
|---|---|---|---|
| 6,288,124 B1 | 9/2001 | Kaddurah-Daouk |
| 6,399,661 B1 | 6/2002 | Golini |
| 6,465,018 B1 | 10/2002 | Tuttle |
| 6,503,951 B2 | 1/2003 | Pischel et al. |
| 6,537,969 B1 | 3/2003 | Blass |
| 6,706,764 B2 | 3/2004 | Kaddurah-Daouk et al. |
| 7,179,477 B2 | 2/2007 | Gupta |
| 7,186,754 B2 | 3/2007 | Kaddurah-Daouk |
| 7,217,423 B2 | 5/2007 | Golz-Berner et al. |
| 7,285,573 B2 | 10/2007 | Kaddurah-Daouk et al. |
| 2002/0035155 A1 | 3/2002 | Kaddurah-Daouk |
| 2002/0049253 A1 | 4/2002 | Kaddurah-Daouk |
| 2002/0098239 A1 | 7/2002 | Kuhrts |
| 2002/0150627 A1 | 10/2002 | Stout et al. |
| 2002/0161049 A1 | 10/2002 | Kaddurah-Daouk et al. |
| 2003/0013633 A1 | 1/2003 | Kaddurah-Daouk |
| 2003/0018082 A1 | 1/2003 | Kaddurah-Daouk |
| 2003/0091669 A1 | 5/2003 | Wang |
| 2003/0232793 A1 | 12/2003 | Kaddurah-Daouk et al. |
| 2004/0029969 A1 | 2/2004 | Blatt et al. |
| 2004/0052749 A1 | 3/2004 | Golz-Berner et al. |
| 2004/0054006 A1 | 3/2004 | Kaddurah-Daouk et al. |
| 2004/0077719 A1 | 4/2004 | Jager et al. |
| 2004/0102419 A1 | 5/2004 | Kaddurah-Daouk et al. |
| 2004/0116390 A1 | 6/2004 | Kaddurah-Daouk |
| 2004/0126366 A1 | 7/2004 | Kaddurah-Daouk et al. |
| 2004/0241197 A1 | 12/2004 | Biergiesser et al. |
| 2004/0258717 A1 | 12/2004 | Sauermann et al. |
| 2005/0142154 A1 | 6/2005 | Blatt et al. |
| 2005/0186158 A1 | 8/2005 | Kaddurah-Daouk |
| 2005/0186193 A1 | 8/2005 | Mishra |
| 2005/0186194 A1 | 8/2005 | Kaddurah-Daouk |
| 2005/0186195 A1 | 8/2005 | Kaddurah-Daouk |
| 2005/0226840 A1 | 10/2005 | Kaddurah-Daouk |
| 2005/0227996 A1 | 10/2005 | Kaddurah-Daouk |
| 2005/0256134 A1 | 11/2005 | Kaddurah-Daouk |
| 2006/0018869 A1 | 1/2006 | Stab et al. |
| 2006/0039887 A1 | 2/2006 | Gupta et al. |
| 2006/0128643 A1 | 6/2006 | Kaddurah-Daouk et al. |
| 2006/0128671 A1 | 6/2006 | Kaddurah-Daouk et al. |
| 2006/0241021 A1 | 10/2006 | Kaddurah-Daouk et al. |
| 2007/0027090 A1 | 2/2007 | Kaddurah-Daouk et al. |
| 2008/0003208 A1 | 1/2008 | Nivaggioli |
| 2008/0119450 A1 | 5/2008 | Kaddurah-Daouk et al. |

FOREIGN PATENT DOCUMENTS

| | | |
|---|---|---|
| FR | 8.293 | 11/1970 |
| WO | 90/09192 | 8/1990 |
| WO | 92/08456 | 5/1992 |
| WO | 92/14697 | 9/1992 |
| WO | 94/16687 | 8/1994 |
| WO | 94/17794 | 8/1994 |
| WO | 95/20950 | 8/1995 |
| WO | 96/14063 | 5/1996 |
| WO | 96/36348 | 11/1996 |
| WO | 97/13507 | 4/1997 |
| WO | 01/54676 | 8/2001 |
| WO | 03/047367 | 6/2003 |

OTHER PUBLICATIONS

Stewart et al, "Type 2 diabetes mellitus, cognitive impairment and dementia," Diabetic Medicine, 1999, vol. 16, pp. 93-112.

Annesley, Thomas M. et al, "Cyclocreatine Phosphate as a Substitute for Creatine Phosphate in Vertebrate Tissues, Energetic Considerations," Biochemical and Biophysical Research Communications, vol. 74 (1): 185-190 (1977).

Annesley, Thomas M. et al, "Formation and Utilization of Novel High Energy Phosphate Reservoirs in Enrich Ascites Tumor Cells," The Journal of Biological Chemistry, vol. 253(22): 8120-8125 (1978).

Beal, M. Flint et al, "Age-Dependent Striatal Exitotoxic Lesions Produced by the Endogenous Mitochondrial Inhibitor Malonate," Journal of Neurochemistry, vol. 61, 1147-1150 (1993).

Beal, M. Flint et al, "Aminooxyacetic Acid Results in Excitotoxin Lesions by a Novel Indirect Mechanism," Journal of Neurochemistry, vol. 57: 1068-1073 (1991).

Beal, M. Flint, "Bioenergetic Approaches for Neuroprotection in Parkinson's Disease," Ann. Neural. vol. 53 (Suppl. 3): S39-S48 (2003).

Beal, M. Flint et al, "Coenzyme Q10 and Nicotinamide Block Striatal Lesions Produced by the Mitochondrial Toxin Malonate," Ann Neurol., vol. 36, 882-888 (1994).

Beal, M. Flint et al, "Coenzyme Q10 attenuates the 1-methyl-4-phenyl-1,2,3,6-tetrahydropyridine (MPTP) induced loss of striatal dopamine and dopaminergic axons in aged mice," Brain Research, vol. 783: 109-114 (1998).

Beal, M. Flint et al, "Coenzyme Q10 in the Central Nervous System and its Potential Usefulness in the Treatment of Neurodegenerative Diseases," Molec. Aspects Med., vol. 18 (Suppl.): 2169-S179 (1997).

Beal, M. Flint, "Does Impairment of Energy Metabolism Result in Excitotoxic Neuronal Death in Neurodegenerative Illnesses?" Ann. Neurol. vol. 31: 119-130 (1992).

Beal, M. Flint "Neurochemistry and Toxin Models in Huntington's Disease," Current Opinion in Neurology, vol. 7: 542-547 (1994).

Bernsen, P.L. J.A. et al, "Treatment of complex I deficiency with riboflavin," Journal of the Neurological Sciences, vol. 118: 181-187 (1993).

Boehm, Ernest A., "The utilisation of creative and it analogues by bytosolic and mitochondrial cratine kinase," Biochimica et Biophysica Acta, vol. 1274: 119-128 (1996).

Brady, Scott T. et al, "Nerve-specific Enclase Creatine Phosphokinase in Axonal Transport: Soluble Proteins and the Axoplasmnic Matrix," Cell, vol. 23: 515-523 (1981).

Brouillet, Emmanuel et al, "Chronic mitochondrial energy impairment produces selective striatal degeneration and abnormal choreiform movement in primates," Proc. Natl. Acad, Sco. USA, vol. 92: 7105-7109 (1995).

Carter Adrian J. et al, "Preincubation with Ceatine Enhances Levels of Creatine Phosphate and Pevents Anoxic Damage in Rat Hippocampal slices," Journal of Neurochemistry, vol. 64: 2691-2699 (1995).

Chmoulovsky, M. et al, "Pre- and Postsynaptic Utilization of ATP and Creatine Phosphate at the Nerve-Electroplaque Junction," Journal of Neurochemistry, vol. 22: 73-75 (1974).

Cramer, Friedrich et al, "Die Synthese der Argininphosphorusaure und die Reaktion von Isoureidophoshonaten mit Aminen," Chem. Ber., vol. 95: 1670-1982 (1962).

Deleon, M. et al, "Identification of Transcriptionally Regluated Genes after Sciatic Nerve Injury," Journal of Neuroscience Research, vol. 29: 437-448 (1991).

Fitch, Coy D. et al, "A Study of Creatine Metabolism in Diseases Causing Muscle Wasting," Journal of Clinical Investigation, vol. 43(3); 444-452 (1964).

Folkers, Karl et al, "Two successful double-blind trials with coenzyme Q10 (vitamin Q10) on muscular dystrophies and neurogenic atrophies," Biochimica et Biophysica Acta, vol. 1271: 281-286 (1995).

Friedhoff, Arnold J. et al, "Creatine Kinase Isoenzyme Associated with Synaptosomal Membrane and synaptic Vesicles," Life Sciences, vol. 20: 867-874 (1977).

Ghorayeb, Imab et al, "Toward a Primate Model of L-Dopa-Unresponsive Parkinsonism Mimicking Striatonigral Degeneration," Movement Disorders, vol. 15(3): 531-536 (2000).

Gold, R. et al, "Phosphorus Magnetic Resonance Spectroscopy in the Evaluation on Mitochondrial Myopathies: Results of a 6-Month Therapy Study with Coenzyme Q," European Neurology, vol. 36: 191-196 (1996).

Goodman, "The Pharmacological Basis of Therapeutics," 6th Edition, Macmillan Publishing Co., Inc., Chapter 1, pp. 5-10 (1980).

Griffiths, Garth R. et al, "Accumulation of Analog of Phosphocreatine in Muscle of Chicks Fed 1- Carboxymethyl-2-minoimidazolidine (cyclocreatine)," The Journal of Biological Chemistry, vol. 251 (7): 2049-2054 (1976).

(56) References Cited

OTHER PUBLICATIONS

Gu, M. et al, "Mitochondrial Defect in Huntington's Disease Caudate Nucleus," Ann. Neurol., vol. 39: 385-389 (1996).

Gurney, Mark E. et al, "Motor Neuron Degeneration in Mice That Express a Human Cu, Zn Superoxide Dismutase Mutation," Science, vol. 264: 1772-1775 (1994).

Hagenfeldt, Lars et al, "Creatine Treatment in Melas," Muscle & Nerve, vol. 10: 1236-1237 (1994).

Hemmer, Wolfram et al, "Creatine Kinase Isoenzymes in Chicken Cerebellum: Specific Localization of Brain-Type Creatine Kinase in Bergmann Blial Cells and Muscle-type Creatine Kinase in Purkinje Neurons," European Journal of Neuroscience, vol. 6: 538-549 (1994).

Hemmer, Wolfram et al, "Functional Aspects of Creatine Kinase in Brian," Dev. Neuroscience, vol. 15: 249-260 (1993).

Henshaw, Ross et al, "Malonate produces striatal lesions by indirect NMDA receptor activation," Brain Research, vol. 647: 161-166 (1994).

Hertz, Leif et al, "Energy Metabolism at the Cellular Level of the CNS," Can. J. Physiol. Pharmacol. vol. 70: S145-S157 (1992).

Hirst, Marion et al, "Creatine and Rigidity," Quarterly Journal of Medicine, vol. 83: 401-418 (1928).

Ikejiri, Y. et al, "Idebenone Improves Cerebral Mitochondrial Oxidative Metabolism in a Patient with MELAS," Neurology, vol. 47:583-585 (1996).

Ito, Masao, "The cellular basis of cerebellar plasticity," Current Opinion in Neurobiology, vol. 1: 616-620 (1991).

Jenkins, Bruce G. et al, "Evidence of Impairment of Energy Metabolism In Vivo in Huntington's Disease Using Localized 1H NMR Spectroscopy," Neurology, vol. 43: 2689-2695 (1993).

Khan, M.A., "Effect of Calcium on Creatine Kinase activity of Cerebellum," Histochemistry, vol. 48: 29-32 (1976).

La Fontaine, Michael A. et al, "Effect of Exogenous and Endogenous Antioxidants on 3-Nitropropionic Acid-induced in Vivo Oxidative Stress and Striatal Lesions: Insights into Huntington's Disease," Journal of Neurochemistry, vol. 75: 1709-1715 (2000).

Langsjoen, Per H. et al, "A Six-Year Clinical Study of Therapy of Cardiomyopathy with Coenzyme A10," Int. J. Tiss. Reac., vol. XII (3): 169-171 (1990).

Langsjoen Per H. et al, "Pronounced Increase of Survival of Patients with Cardiomyopathy when Treated with Coenzyme A10 and Conventional Therapy," Int. J. Tiss. Reac., vol. XII (3): 163-168 (1990).

Lee, Wang-Tso et al, "Magnetic resonance imaging and spectroscopy in assessing 3-nitropropionic acid-induced brain lesions: an animal model of Huntington's Disease," Progress in Neurobiology, vol. 72: 87-110 (2004).

Lillie, James W. et al, "Cyclocreatine (1-Carboxymethyl-2-iminolmidazolidine) Inhibits growth of a Broad Spectrum of Cancer Cells Derived from Solid Tumors," Cancer research, vol. 53: 3172-3178 (1993).

Lim, L. et al, "Neurone-Sepcific Enolase and Creatine Phosphokinase are Protein Components of Rat Brain Synaptic Plasmas Membranes," Journal of Neurochemistry, vol. 41: 1177-1182 (1983).

Lopresti, Patrizia et al, "Direct determination of creatine kinase equilibrium constants with creatine orcyclocreatine as substrate," Biochimica et Biophysica Acta, vol. 998: 317-320 (1989).

Lowe, Gordon et al, "Evidence for an Associative Mechanism in the Phosphoryl Transfer Step Catalyzed by Rabbit Muscle Creatine Kinase," The Journal of Biological Chemistry, vol. 255 (9): 3944-3951 (1980).

Maker, Howard S. et al, "Regional Changes in Cerebellar Creatine Phosphate Metabolism During Late Maturation," Experimental Neurology, vol. 38: 395-300 (1973).

Malcon, Cesar et al, "Neuroprotective effects of creatine administration against NMDA and malonate toxicity," Brain Research, vol. 860: 195-198 (2000).

Manos, Patricia, et al, "Creatine Kinase Activity in Postnatal Rat Brain Development and in Cultured Neurons, Astrocytes, and Oligodendrocytes," Journal of Neurochemistry, vol. 56: 2101-2107 (1991).

Manzoli, U. et al, "Coenzyme Q10 in Dilated Cardiomyopathy," Int. J. Tiss. Reac., vol. XII (3) 173-178 (1990).

Marletta, Michael A. et al, "Affinity Labeling of Creatine Kinase by N-(2,3-Epoxypropyl)-N-amidinoglycine," The Journal of Biological Chemistry, vol. 254 (6): 1879-1979 (1979).

McLaughlin, Alan C. et al, "Specificity of Creatine Kinase for Guanidino Substrates," The Journal of Biological Chemistry, vol. 247 (13): 4382-4388 (1972).

Mitchell, Todd R. et al, "Striatal Oxidative Metabolic Failure in an Improved Rat Model of Huntington's Disease Monitored Via HR-MAS Proton Magnetic Resonance Spectroscopy at 11.7T," Proc ISMRM, vol. 10: 102 (2002).

Molloy, George R. et al, "Rat Brain Creatine Kinase Messenger RNA Levels are High in Primary Cultures of Grain Astrocytes and Oligodendrocytes and Low in Neurons," Journal of Neurochemistry, vol. 59: 1925-1932 (1992).

Morisco, C. et al, "Effect of Coenzyme Q10 therapy in patients with congestive heart failure: a long-term multicenter randomized study," Clincial Investigator, vol. 71: S134-S136 (1993).

Newman, Eric A., "Regulation of potassium levels by glial cells in the retina," Trends in Neuroscience, vol. 8: 150-159, (1985).

Oblinger, Monica M et al, "Cytotopic Differences in the Protein Composition of the Axonally Transported cytoskeleton in Mammalian Neurons," The Journal of Neuroscience, vol. 7(2): 453-462 (1987).

Penn, A.M.W. et al, "MELAS Syndrome with Mitochondrial tRNA Lue (UUR) Mutation: Correlationo f clinical state, nerve conduction, and muscle 31P magnetic resonance spectroscopy during treatment with nicotinamide and riboflavin,".

Pettegrew, Jay W. et al, "Alterations of Cerebral Metabolism in Probable Alzheimer's Disease: A Preliminary Study," Neurobiology of Aging, vol. 15(1): 117-132 (1994).

Rehunen, P. et al, "High-Energy Phosphate Comounds in Slow-Twitch and Fast-Twitch Muscle Fibres," Journal of Neurological Sciences, vol. 67: 299-306 (1985).

Reichenbach, Andreas, "Glial K+ Permeability and CNS K+ Clearance by Diffusion and Spatial Buffering," Annals of the New York Academy of Sciences, vol. 633: 272-286 (1991).

Reinhold, John g. et al, "The chemical composition of voluntary muscle disease: a comparison of progressive muscular dystrophy with other diseases together with a study of effect of glycine and creatine therapy," J. Clin. Invest. vol. 17(4): 377-383 (1938).

Roberts, Jeffrey J. et al, "Feeding a creatine analogue delays ATP depletion and onset of rigor in ischemic heart," Am. J. Physiol. Heart Circ. Physiol, vol. 243(6): H911-H916 (1982).

Roberts, Jeffrey J. et al, "Higher Homolog and N-Ethyl Analog of Creatine as Synthetic Phosphagen Precursors in Brain, Heart, and Muscle, Repressors in Liver Amidinoltransferase, and Substrates for Creatine Catabolic Enzymes," The Journal of biological Chemistry, vol. 260 (25): 13502-13508 (1985).

Roberts, Jeffrey J. et al, "Synthesis and Accumulation of an Extremely Stable High Energy Phosphate Compound by Muscle, Heart, and Brain of Animals Fed by the Creatine Analog, 1-Carboxyethyl-2-iminoimidazolidine (Homocyclocreatine)," Archives of Biochemistry of Biophysics, vol. 220(2): 563-571 (1983).

Rowley, Gerald L. et al, "On the Specificity of Creatine Kinase, New Glycocyamines and Glycocyamine Analogs Related to Creatine," Journal of American Chemical Society, vol. 93 (21): 5542-5551 (1971).

Rudinger, J., "Characteristics of the amino acids as components of a peptide hormone sequence," Peptide Hormones, J. Parsons, Ed., Chapter 1, pp. 1-6 (1976).

Schiffman, Raphael et al, "Childhood Ataxia with Diffuse Central Nervous System Hypomyelination," Ann. Nuerol., vol. 35: 331-340 (1994).

Schultheiss, Karl et al, "Effects of Creatine on Synthesis and Release of y-[3H]Aminobutyric Acid," Journal of Neurochemistry, vol. 54: 1858-1863 (1990).

(56) References Cited

OTHER PUBLICATIONS

Schulz, Jorg B. et al, "Blockade of Neuronal Nitric Oxide Synthase Protects against Excitotoxicity in Vivo," The Journal of Neuroscience, vol. 15 (1): 8419-8429 (1995).
Schulz, Jorg B. et al, "Coenzyme Q10 and Nicotinamide and a Free Radical Spin Trap Protect Against MPTP Neurotoxicity," Experimental Neurology, vol. 132: 279-283 (1995).
Schulz, Jorg B. et al, "Inhibition of Neuronal Nitric Oxide Synthase by 7-Nitroindazole Protects Against MPTP-Induced Neurotoxicity in Mice," Journal of Neurochemistry, vol. 64: 936-939 (1995).
Serebruany, Victor J. et al, "Hemostatic Changes after Dietary Coenzyme Q10 Supplementation in Swine," Journal of Cardiovascular Pharmacology, vol. 28: 175-181 (1996).
Stadhouders, Ad M. et al, "Mitochondrial creatine kinase: A Major constituent of pathological inclousions seen in mitochondrial myopathies," Proc. Natl. Acad. Sci. USA, vol. 91: 5089-5093 (1994).
Strong, Michael J. et al, "Creatine and Coenzyme Q10 in the Treatment of ALC," Amyotrophic Lateral Sclerosis, vol. 1 (Suppl): 17-20 (2000).
Vis, J.C. et al, "The mitochondrial toxin 3-nitropropionic acid induces differential expression patterns of apoptosis-related markers in rat striatum," Neuropathy and Neurobiology, vol. 27: 68-76 (2001).
Walker, James B., "bioenergetic engineerings with guanidino compounds. Loading tissues with extended-range synthetic thermodynamic buffers," Guanidino Compounds in Biology and Medicine, eds. by P.P. De Deyn. B. Marescau, V. Stalon and I.A. Qureshi, John Libby & Company Ltd. pp. 187-194 (1992).
Wang, "Synthesis and Properties of N-Acetimidoyl Derivatives of Glycine and Sarcosine," J. Org. Chem. vol. 39 (24): 3591-3594 (1974).
Woznicki, Dennis T. et al, "Utilization of Cyclocreatine Phosphate, an Analogue of Creatine Phosphate, by Mouse Brain During Ischemia and its Sparing Action on Brain Energy Reserves," Journal of Neurochemistry, vol. 34 (5): 1247-1253 (1980).
Loike, John D. et al, "Creatine uptake, metabolism, and efflux in human monocytes and macrophages," American Physiological Society, c128-135 (1986).
Rae, C. et al, "Brain Biochemistry in Williams Syndrome: Evidence for a role of the cerebellum in cognition?" American Academy of Neurology, vol. 51: 33-40 (1998).
Braissant, Olivier et al, "Endogenous synthesis and transport of creatine in the rat brain, an in situ hybridization study," Molecular Brain Research, vol. 86: 193-201 (2001).
Casanova, E. et al, "A CamKila iCRE BAC Allows Brain-Specific Gene Inactivation," Technology Report, Genesis vol. 31: 37-42 (2001).
Moll, Gunther H. et al, "Children with Comorbid Attention-Deficit-Hyperactivity Disorder and Tic Disorder: Evidence for Additive Inhibitory Deficits within the Motor System," Annals of Neurology, vol. 49 (4): 393-414 (2001).
Conn, Rex B. Jr., "Fluorimetric Determination of Creatine," Clinical Chemistry, vol. 6: 537-548 (1960).
Dringen, Ralf et al, "Metabolism of Glycine in Primary Astroglial Cells: Synthesis of Creatine, Serine, and Glutathione," Journal of Neurochemistry, vol. 70 (2): 835-840 (1998).
Fitch, Coy D. et al, "Inhibition of Creatine and Phosphocreatine Accumulation in Skeletal Muscle and Heart," Metabolism, vol. 29 (7): 686-690 (1980).
Rae, Caroline et al, "Is pH a Biochemical Marker for IQ?" Proceedings: Biological Sciences, vol. 263 (1373): 1061-1064 (1996).
Ku, Chaun-Pao et al, "Creatine and Creatinine Transport in Old and Young Human Red Blood Cells," Biochimica et Biophysica Acta, vol. 60: 212-227 (1980).
Salamons, Gaija S. et al, "X-Linked Creatine-Transporter Gene (SLC6A8) Defect: A New Creatine Deficiency Syndrome," Am. J. Hum. Genet., vol. 68: 1497-1500 (2001).
Sauer, Brian, "Inducinle Gene Targeting in Mice Using the Cre/lox System," A Companion to Methods in Enzymology, vol. 14:381-392 (1998).
Tracey, Irene et al, "Brain abnormalities in Duchenne muscular dystrophy: phosphorus-31 magnetic resonance spectroscopy and neuropsychological study," The Lancet, vol. 345: 1260-1264 (1995).

* cited by examiner

METHODS OF TREATING COGNITIVE DYSFUNCTION BY MODULATING BRAIN ENERGY METABOLISM

RELATED APPLICATION

This application is a continuation in part of application Ser. No. 13/347,867, filed Jan. 11, 2012.

BACKGROUND OF THE INVENTION

Creatine is synthesized mainly in liver and kidney. L-arginine:glycine amidinotransferase (AGAT; EC 2.1.4.1) is involved in the formation of guanidinoacetate (GAA) from arginine and glycine. GAA is methylated by S-adenosyl-L-methionine:N-guanidinoacetate methyltransferase (GAMT; EC 2.1.1.2) to form creatine. While some creatine can come from the diet, about 1-2 grams of creatine is synthesized in liver and kidney per day. Creatine, as a dietary component, is found in many red meats and is readily absorbed from the gut. It is transported through the bloodstream to the target tissues, where it is taken up, against a large concentration gradient, by a saturable, $Na^+$ dependent creatine transporter that spans the plasma-membrane. Inside the cell, creatine takes part in the energy metabolism through the creatine kinase reaction and it is metabolized at a constant rate to creatinine, which is excreted through the kidneys. About 3% of the total body creatine is lost per day in this way. This 3% is independent of the amount of creatine in the body, so if there is creatine supplementation that increases total body creatine, the creatinine excretion is predicted to be increased as well.

Studies on creatine transport have focused on the influx of creatine in several different tissues (Ku, C.-P. *Biochim. Biophys. Acta.* 600:212-227, 1980; Loike, J. D., *Am. J. Physiol.* 251:C128-C135, 1986; Möller, A. *J. Neurochem* 62:544-550, 1989) (See FIG. 3-6). transport is highly specific, $Na^+$ dependent, and sensitive to metabolic inhibitors (Fitch, C. D. et al. *Neurology* 13:32-42, 1968; Fitch, C. D. *Metabolism* 29:686-690, 1980; Loike, J. D. et al. *Clinical Research* 34:548, 1986; Loike, J. D. et al. *Proc. Natl. Acad Sci*, USA. 85: 807-811, 1988; Möller, A. *J. Neurochem* 52: 544-550; 1989). In the rat blood stream, the concentration of creatine is about 100 µM (Syllm-Rapoport, I. et al. *Acta Biol. Med Germ.* 40:653-659, 1980) while the intracellular concentration is several milimolar. Data from human monocytes and macrophages shows the $K_m$ in the normal cells to be approximately 30 µM. The creatine concentration in human serum is in the range of 50 µM. Thus, the transporter in these human cells can respond to physiological fluctuations in creatine by altering the activity of the transporter.

SUMMARY OF THE INVENTION

The present invention relates to a method for treating or preventing cognitive dysfunction in a subject having a creatine deficiency in the brain due to a creatine transporter dysfunction which method comprises administering to such subject an effective amount of cyclocreatine or a pharmaceutically acceptable salt thereof.

DETAILED DESCRIPTION OF THE INVENTION

Methods for Treating Cognitive Dysfunction by Modulating Brain Energy Metabolism Energy metabolism impairment is believed to be a component in cognitive dysfunction, behavioral and expressive deficiencies (Cecil, K. M. et al. *Ann Neurol* 49:401-4, 2001; Salomons, G. S. et al. *Am J Hum Genet* 68: 1497-500, 2001). The brain is dependent upon glucose oxidation for energy metabolism, and, to a lesser extent, it is also able to use ketone bodies as an energy source under certain conditions. The brain tightly controls energy metabolism and glucose oxidation to maintain an adequate energy supply.

In an embodiment, the invention pertains, at least in part, to a method for treating a cognitive dysfunction in a subject by modulating, e.g. increasing, brain energy metabolism. Brain energy metabolism can be modulated by administering to the subject an effective amount of cyclocreatine or a pharmaceutically acceptable salt thereof. In a further embodiment, the subject's brain energy metabolism is normal, after the administration of the cyclocreatine or pharmaceutically acceptable salt thereof.

The term "brain energy metabolism" includes aerobic metabolism, anaerobic metabolism, glycolytic metabolism, mitochondrial metabolism, and the generation of energy buffers such as adenylate kinase and creatine kinase, which generate energy in the brain. It also includes energy metabolism in the subject's neural or glial cells. Brain energy metabolism can be increased by increasing the ATP or creatine phosphate concentration, or by decreasing the concentration of ADP, GDP, AMP, or other mono- or di-phosphorylated nucleotides. Brain metabolism can be increased by the administration of the cyclocreatine compounds of the invention.

The term "cognitive dysfunction" includes learning dysfunction, autism, attention deficit disorders, fragile X syndrome, obsessive-compulsive disorders, speech dysfunction, speech deficits, learning disabilities, impaired communication skills, mental retardation, low IQ, short term memory dysfunction, spatial learning dysfunction, and cognitive dysfunction associated with inborn errors of metabolism affecting the brain (such as, but not limited to creatine transporter dysfunction, 1-arginine:glycine amidinotransferase (AGAT) deficiency and guanidinoacetate n-methyltransferase (GAMT) deficiency). Cognitive dysfunction also includes states of altered cognitive, expressive and behavioral function. In one embodiment, the term "cognitive dysfunction" does not include neurodegenerative disorders.

The term "subject" includes cells and animals capable of suffering from cognitive dysfunction. It includes organisms which are at risk of suffering from cognitive dysfunction or who are currently suffering from cognitive dysfunction. Examples of organisms include both transgenic and non-transgenic rodents, goats, pigs, sheep, cows, horses, squirrels, bears, rabbits, monkeys, chimpanzees, gorillas, frogs, fish, birds, cats, dogs, ferrets, and, preferably, humans.

The term "creatine transporter dysfunction" includes a disorder characterized by any one of: an inborn error of creatine synthesis that affects transporter function; an inborn error of the creatine transporter, or any other aberrant creatine transporter morphology and/or function in the brain. The aberrant creatine transporter function may cause the subject to suffer from a low concentration of creatine in the brain of a subject suffering from creatine transporter dysfunction. In this disorder, impaired energy metabolism is believed to be associated with impaired learning dysfunction and cognitive function. It was found that treatments of similar neurological or cognitive dysfunctions do not tend to target improving metabolism and/or energy metabolism of the brain, neural cells, or glial cells. The invention also pertains, at least in part, to methods of treating a subject with a creatine transporter deficiency in the brain.

The term "X-linked creatine transporter deficiency" refers specifically to an X-linked creatine transporter deficiency caused by absence of, or a mutation in SLC6A8, which is located on human chromosome Xq28. Mutations in this gene result in a more severe syndrome in males than in female carriers. X-linked creatine transporter deficiency is also referred to herein as CTD.

The term "treating" includes the alleviation of diminishment of one or more symptoms of the disorder, disease, or dysfunction being treated. For example, the cognitive dysfunction may be treated by improving cognitive function, improving expressive function, decreasing seizure activity, improving behavioral parameters, increasing intelligence, or improving motor function.

Pharmaceutical Compositions for the Treatment of Cognitive Dysfunctions

Cyclocreatine or any pharmaceutically acceptable salt thereof may be administered to the subject in combination with a pharmaceutically acceptable carrier.

The phrase "pharmaceutically acceptable carrier" includes a pharmaceutically acceptable material, composition or vehicle, such as a liquid or solid filler, diluent, excipient, solvent or encapsulating material, involved in carrying or transporting a compound(s) of the invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation and not injurious to the subject. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

As set out above, cyclocreatine contains a basic functional group and is therefore capable of forming pharmaceutically acceptable salts with pharmaceutically acceptable acids. The term "pharmaceutically acceptable salts" in this respect, refers to the relatively non-toxic, inorganic and organic acid addition salts of compounds of the invention. These salts can be prepared in situ during the final isolation and purification or by separately reacting purified cyclocreatine in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, e.g., Berge et al (1977) "Pharmaceutical Salts," *J. Pharm. Sci.* (66:1-19).

In other cases, cyclocreatine is capable of forming pharmaceutically acceptable salts with pharmaceutically acceptable bases. The term "pharmaceutically acceptable salts" in these instances refers to the relatively non-toxic, inorganic and organic base addition salts of compounds of the invention. These salts can likewise be prepared in situ during the final isolation and purification of cyclocreatine, or by separately reacting the carbonate or bicarbonate or a pharmaceutically acceptable metal cation, with ammonia, or with a pharmaceutically acceptable organic primary, secondary or tertiary amine. Representative alkali or alkaline earth salts include ethylamine, diethylamine, ethylenediamine, ethanolamine, diethanolamine, piperazine and the like.

Wetting agents, emulsifiers, and lubricants, such as sodium lauryl sulfate and magnesium stearate, as well as coloring agents, release agents, coating agents, sweetening, flavoring and perfuming agents, preservatives and antioxidants can also be present in the invention.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect.

Methods of preparing these formulations or compositions include the step of bringing into association cyclocreatine or a pharmaceutically acceptable salt thereof with the carrier and, optionally, one or more accessory ingredients. In general, the formulations are prepared by uniformly and intimately bringing into association said cyclocreatine compounds of the invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia and tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of cyclocreatine or a pharmaceutically acceptable salt thereof as an active ingredient. A formulation of the invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the invention, such as dragees, capsules, pills and granules, may optionally be scored or prepared with coatings and shells, such as enteric coatings and other coatings as well known in the pharmaceutical-formulating art. They may also be formulated so as to provide slow or controlled release of the active ingredient therein using, for example, hydroxyproylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes.

The active ingredient can also be in micro-encapsulated form, if appropriate, with one or more of the above-described excipients.

Liquid dosage forms for oral administration of cyclocreatine or pharmaceutically acceptable salts thereof include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters or sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrstalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing cyclocreatine or a pharmaceutically acceptable salt thereof with one or more suitable non-irritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the invention which are suitable for vaginal administration also include pessaries, tampons, creams, gels, pastes, foams or spray formulations containing such carriers as are known in the art to be appropriate.

Dosage forms for the topical or transdermal administration of cyclocreatine or a pharmaceutically acceptable salt thereof include powders, sprays, ointments, pastes, creams, lotions, gels, solutions, patches and inhalants. The active compound may be mixed under sterile conditions with pharmaceutically acceptable carriers, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to cyclocreatine or a pharmaceutically acceptable salt thereof, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of cyclocreatine or a pharmaceutically acceptable salt thereof to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Pharmaceutical compositions of this invention suitable for parenteral administration comprise cyclocreatine or a pharmaceutically acceptable salt thereof in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a compound, it is desirable to slow the absorption of the compound from subcutaneous or intramuscular injection. This may be accomplished by the use of a liquid suspension of crystalline or amorphous material having poor water solubility. The rate of absorption of the compound then depends upon its rate of dissolution which, in turn, may depend upon crystal size and crystalline form. Alternatively, delayed absorption of a parenterally-administered compound is accomplished by dissolving or suspending the compound in an oil vehicle.

Injectable depot forms are made by forming microencapsule matrices of the compound of the invention in biodegradable polymers such as polylactide-polyglycolide. Depending on the ratio of compound to polymer, and the nature of the particular polymer employed, the rate of compound release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the invention may be given orally, parenterally, topically, or rectally. They are, of course, given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection and infusion.

The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, cyclocreatine or a pharmaceutically acceptable salt thereof, which may be used in a suitable hydrated form, and/or the pharmaceutical compositions of the invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular subject, composition, and mode of administration, without being toxic to the subject.

The selected dosage level will depend upon a variety of factors including the activity of the formulation employed, the route of administration, the time of administration, the rate of excretion of the particular compound being employed, the duration of the treatment, other drugs, compounds and/or materials used in combination with the particular formulation employed, the age, sex, weight, condition, general health and prior medical history of the subject being treated, and like factors well known in the medical arts.

A physician or veterinarian having ordinary skill in the art can readily determine and prescribe the effective amount of the pharmaceutical composition required. For example, the physician or veterinarian could start doses of cyclocreatine or a pharmaceutically acceptable salt thereof employed in the pharmaceutical composition at levels lower than that required in order to achieve the desired therapeutic effect and gradually increase the dosage until the desired effect is achieved.

The regimen of administration can affect what constitutes an effective amount. The formulation of the invention can be administered to the subject either prior to or after the onset of a cognitive dysfunction. Further, several divided dosages, as well as staggered dosages, can be administered daily or sequentially, or the dose can be continuously infused, or can be a bolus injection. Further, the dosages can be proportionally increased or decreased as indicated by the exigencies of the therapeutic or prophylactic situation.

The compositions useful in the methods of the invention comprise an effective amount of cyclocreatine or a pharmaceutically acceptable salt thereof to treat or prevent cognitive dysfunction in a subject having a creatine deficiency in the brain caused by a creatine transport dysfunction. The compositions further may comprise a pharmaceutically acceptable carrier.

The term "effective amount" includes the amount of cyclocreatine or a pharmaceutically acceptable salt thereof necessary for the treatment, amelioration, or prevention of at least one symptom of cognitive dysfunction.

In another embodiment, the invention pertains to a method for treating cognitive dysfunction in a subject, by increasing the concentration of cyclocreatine in the subject's brain.

In another embodiment, the invention pertains to a method for treating cognitive dysfunction in a subject, by increasing the concentration of ATP in the subject's brain.

Methods for Treating Cognitive Dysfunction by Modulating Brain pH

The creatine kinase reaction is believed to be pH sensitive; it is believed that as the concentration of H+ ions increases, creatine phosphate hydrolysis is also increased. The creatine kinase and creatine phosphate system is sometimes considered to be a pH buffer in cells. For example, in periods of ischemia and acidosis, the acidosis is sometimes tempered (buffered) by the consumption of H* ions during the hydrolysis of creatine phosphate. Brain acidosis has been associated with lower IQ (Rae, C. et al, *Neurology* 51: 33-40, 1998; Rae, C. et al., *Proc R Soc Lond B Biol Sci* 263: 1061-4, 1996; Tracey, I. et al, Lancet 345: 1260-4, 1995).

Not to be limited by theory, the lack of brain creatine/creatine phosphate may impede the brain's ability to buffer pH changes and thereby result in acidosis. Although brain pH has not yet been correlated to IQ in this subject population, brain metabolism (pH and creatine) has been associated with clinical conditions where cognitive function is impaired (Cecil, K. M. et al, *Ann Neurol* 49: 401-4, 2001; Rae, C. et al *Neurology* 51: 33-40, 1998; Rae, C. et al *Proc R Soc Lond B Biol Sci* 263: 1061-4, 1996; Salomons, G. S. et al, *Am J Hum Genet* 68: 1497-500, 2001). Abnormal pH may cause abnormal brain metabolism, because many metabolic enzymes are pH sensitive, and abnormal metabolism may alter pH or pH buffering.

In one embodiment, the invention pertains to methods for treating cognitive dysfunction in a subject, by modulating the subject's brain pH, such that the cognitive dysfunction in the subject is treated. The subject's brain pH can be modulated by, for example, altering brain energy metabolism by the administration of cyclocreatine or a pharmaceutically acceptable salt thereof, as described above.

Methods of Diagnosing and Monitoring Cognitive Dysfunction

In another embodiment, the invention pertains to methods and kits for diagnosing cognitive dysfunction or abnormal brain energy metabolism by measuring blood, serum or plasma intracellular and extracellular metabolite concentrations.

In yet another embodiment, the invention pertains to methods and kits for the diagnosis of errors in creatine metabolism and creatine transport, by measuring the level of creatine or another brain metabolite in the blood serum, plasma, or urine. The diagnostic test may be used to diagnose the condition (or carrier status) and assess therapeutic treatments of subjects who have defects in creatine metabolism or transport and to follow the course of the disease.

In yet another embodiment, the invention pertains to a method for diagnosing errors in creatine metabolism and creatine transport by measuring creatine in the blood cell and in the serum/plasma. The diagnostic test may be used to diagnose the disease or carrier status of the disease and to assess the whole body status of creatine and metabolites, as well as the intracellular creatine and metabolites. The blood cells (red blood cells, white blood cells, etc.) will reflect the transport activity and metabolic changes occurring in the brain and other tissues.

In yet another embodiment, the invention pertains to a method for diagnosis of cognitive dysfunction in a subject, by measuring the concentration of metabolites of creatine in a body sample. The body sample can be from the subject's blood stream, whole blood, blood cells, serum, plasma, tissue biopsy, cerebral spinal fluid, or other diagnostic samples. Examples of creatine metabolites include, but are not limited to, creatine, creatinine, guanidine, guanidine acetic acid, arginine, methionine, homocistine, phosphocreatine and the relative ratios therein. Other metabolites and ratio comparisons will be known to those experienced in the art.

In another embodiment, the invention pertains to a method for diagnosing diseases of creatine transport. The method includes measuring the intracellular creatine in a body sample (e.g., the subject's blood cells (RBC, WBC, etc.) or biopsy from the subject (fibroblast, skin, muscle, brain, etc.)). The method can be used to diagnose the condition (including carrier status), and assess therapeutic treatments of subjects who have defects in creatine metabolism or transport and to follow the course of the disease. Creatine levels can be detected using any method known in the art, such as NMR, MRS, HPLC, antibodies, enzyme linked assays, and spectrophotometric assays.

In another embodiment, the invention pertains to method for diagnosing creating transport dysfunction by measuring the level of the creatine transporter protein or protein fragments or derivatives thereof. The measurement of the creatine transporter protein can be accomplished by western blot, southern blot, oligos or ELISA. The tests can be done with blood cells, skin cells or other biopsy material known to those skilled in the art.

In another embodiment, the invention includes a method for diagnosing a cognitive dysfunction by using a blood or blood urine test to measure serum and cellular metabolites relevant to brain energy metabolism. Creatine has been measured in the serum and blood cells, and it appears to correlate with the changes seen in the subjects. The results from these studies suggest that the blood and urine tests are an index of transporter activity. Also, the difference in circulating creatine in the serum and the concentration in the blood cells may be a quantifiable index of the activity of the creatine transporter. For example, total creatine concentration in the red blood cell when it is released from the bone marrow may be about 1 mm while serum free creatine is about 50 micro molar. If it is assumed that it will take about 30 days for the blood cells to lose their original creatine, and the average red blood cell "lives" 100 days, then there will be decreased creatine in the blood cells, or decreased blood cell: serum ratio. The red blood cell creatine is predicted to be decreased because of decreased creatine transport activity.

In another embodiment, the invention pertains to a method for determining a subject's tolerance to the administration of a creatine compound. The creatine tolerance test comprises comparing pre-oral creatine compound levels to post oral creatine compound levels. The method includes measuring the amount of creatine compound increase in the serum and in the blood cells. It is believed that subject with a creatine transporter defect, or absence, would have impaired increases in the blood cell creatine compound concentration.

There are currently no commercial kits to diagnose creatine transporter dysfunction. All work to date has been accomplished by those experienced in the art to diagnose these subjects and carriers on a case-by-case basis with multiple modalities (MRS/MRI/Western-blot, etc.). Creatine transporter deficiency results from a defect in creatine transporter caused by SLC6A8 deficiency, such that creatine cannot enter the brain's cells, whereas the other two known creatine deficiency syndromes, 1-arginine: glycine amidinotransferase (AGAT) deficiency and guanidinoacetate n-methyltransferase (GAMT) deficiency, are caused by defects in the enzymes that synthesize creatine In patients, creatine deficiency syndromes have several common clinical manifestations, including cognitive dysfunction with mental retardation, poor language skills, and autism spectrum disorders.

Creatine kinase knock-out mice are reported in the academic literature; however if such a disorder were to exist in humans it would be exceeding rare since both kinase genes would have to be affected. Whereas AGAT and GAMT deficiencies have been identified in about 100 patients worldwide, CRT deficiency is described as the second-most common cause of X-linked mental retardation, with an estimated 42,000 individuals affected in the US and approximately 1 million worldwide. Because SLC6A8 is located on human chromosome Xq28, mutations in this gene result in a more severe syndrome in males than in female carriers. Patients with AGAT deficiency or GAMT deficiency have been successfully treated with creatine supplementation, which reverses some symptoms, as well as other supplements, which are needed to manage buildup of intermediate metabolites; however, as has been previously demonstrated by the present investigators, patients with CRT deficiency are not successfully treated with creatine supplementation. Creatine is found in blood and cerebrospinal fluid (CSF), but is not able to enter brain cells—the cell membranes are an effective barrier to creatine transport.

In a further embodiment, the invention pertains to a method for diagnosing cognitive dysfunction, by measuring brain and blood energy metabolism/metabolites. It is believed that by measuring brain and blood energy metabolism/metabolites the therapeutic efficacy of the therapeutic strategies can be assessed.

The strategy for the treatment of the subject may depend on the particular subject and the particular cognitive dysfunction. For example, a heterozygous female carrier of X-linked creatine transporter deficiency can benefit from administration of cyclocreatine to increase cognitive function. Increased cognitive function may be manifested as increased IQ or expressive improvements. Second, the males with X-linked creatine transporter deficiency can benefit from cyclocreatine administration, and third, Subjects without the creatine transporter protein can also benefit from the cyclocreatine therapy.

Models of Cognitive Dysfunction

In an embodiment, the invention pertains to a method of modeling neurological disorders by impairing energy metabolism in the brain of an animal model or in cells. The animal or cellular model may be engineered to decrease phosphorylation potential, block substrate utilization, etc.

In another embodiment, the invention pertains, at least in part, to brain energy metabolism models of human cognitive dysfunction. The models may have altered creatine concentration or metabolism.

The animal models may have deleted or modulated creatine transport or metabolism in their brains. Cells and cell cultures from these animals may also be used to model and correlate to the cognitive dysfunction. The animal models, cells, and cell lines can be used for testing therapies. In addition, cells from subjects suffering from neurological diseases can also be used to model and study cognitive dysfunction, e.g., to identify novel therapies. The cell lines generated from any one of these models may be immortalized.

EXAMPLES

Aspects of the present subject invention will be better understood by reference to the following examples which are offered by way of illustration not limitation.

Example 1

This example illustrates that administration of creatine to a male with X-linked creatine transporter deficiency (CTD) fails to increase brain creatine or to ameliorate clinical symptoms associated with decreased brain levels of creatine.

Figure 1A:
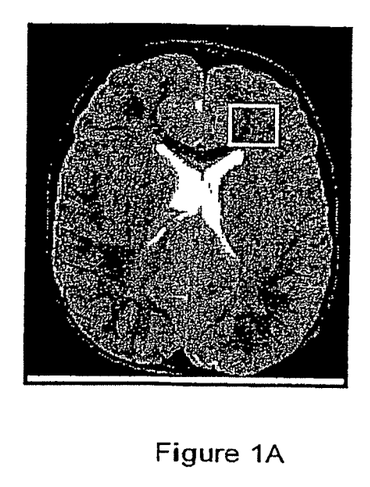
FIG. 1A is a digital image of a MRI of a subject's brain. The subject was subsequently diagnosed with X-linked creatine transporter deficiency.
Figure 1B:
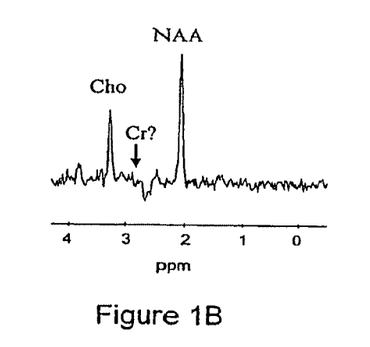
FIG. 1B is a Long Echo $^1H$ MR Spectrum of the subject's brain. The inset box of the MRI (FIG. 1A) shows the voxel where the spectrum was obtained. The white matter shows a profound lack of creatine resonance.
Figure 2:
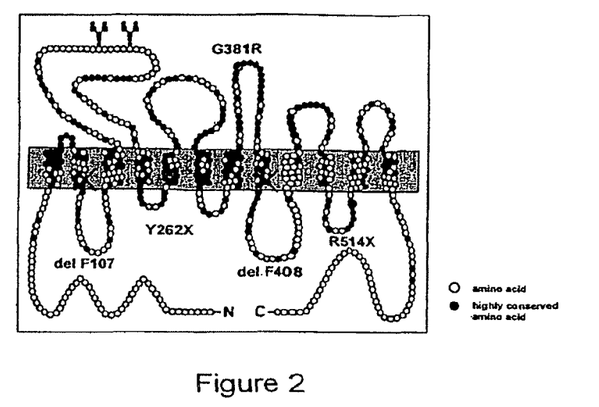
FIG. 2 is a schematic representation of mutations that have been observed in SLC6A8/CRTRI, the creatine transporter protein.

An 8-year old boy with creatine deficiency of the brain was diagnosed by proton MR Spectroscopy, as shown in FIGS. 1A and 1B. Upon further analysis, it was found that he has a nonsense mutation in the X-linked Creatine Transporter gene (CT1;SLC6A8) resulting in a shortened Cr Transporter protein as shown in FIG. 2. Several female family members were identified as heterozygote carriers of this disorder, and appear to have decreased Cr. The boy had severe expressive dysphasia with other cognitive functions less affected.

The boy was treated with increasing doses of creatine to 750 mg/kg/day without clinical or spectroscopic ($^1$H MRS) improvement. In the absence of demonstrable benefit, the creatine treatment was discontinued after 6 months.

Example 2

This example sets forth and validates a murine model for CTD, and demonstrates that administration of cyclocreatine to a subject results in substantial improvement in cognitive dysfunction associated with CTD. The present investigators developed murine models to allow analysis of data related to creatine transporter dysfunction. Via specific models, data is indicated below showing: (a) a successful KO model has been produced (CRT KO mice lack the SLC6A8 creatine transporter gene (the creatine transporter gene)); (b) the CRT KO mice are characterized by significantly lower levels of creatine in the brain and urine, but their levels of creatine in other organs are normal; and (c) supplementation with cyclocreatine results in significant improvement in learning and memory. Additional details of the background and methodology may be found in "Cyclocreatine treatment improves cognition in mice with creatine transporter deficiency" *J Clin Invest.* 122(8): pp 2837-2846 (2012), the entire disclosure of which is incorporated herein by this reference.

Figure 3:
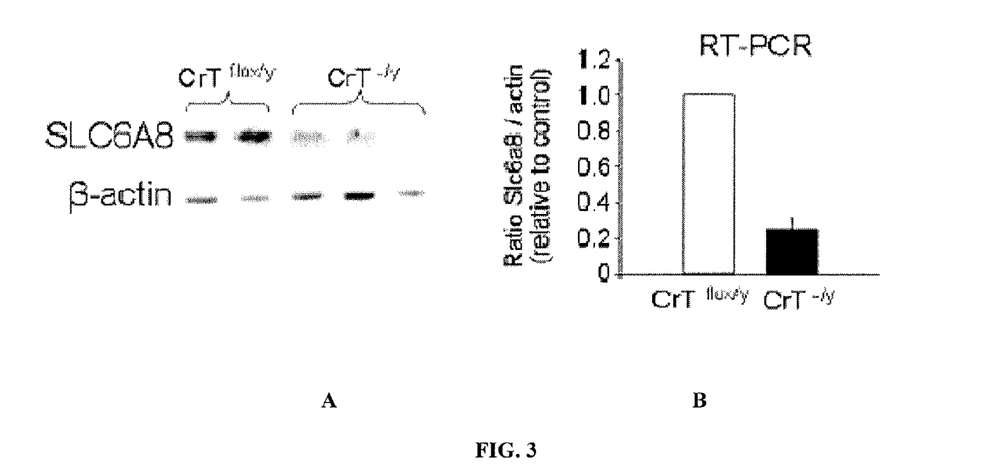
FIG. 3 (A and B) show SLC6A8 levels in CRT KOs versus controls using PCR and actin controls.
Figure 4:
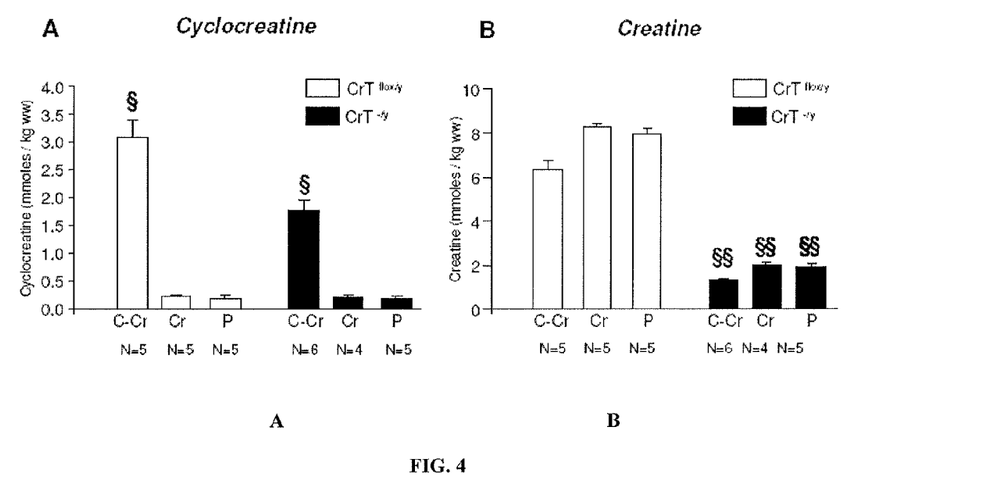
FIG. 4 (A and B) shows cyclocreatine and creatine levels in CRT KO and control mice.
Figure 5:
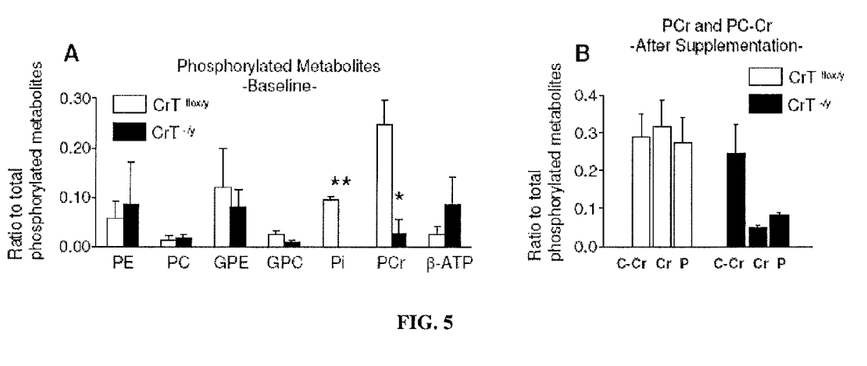
FIG. 5 (A and b) are representations of data collected regarding metabolites in CRT KO mice versus controls.
Figure 6:
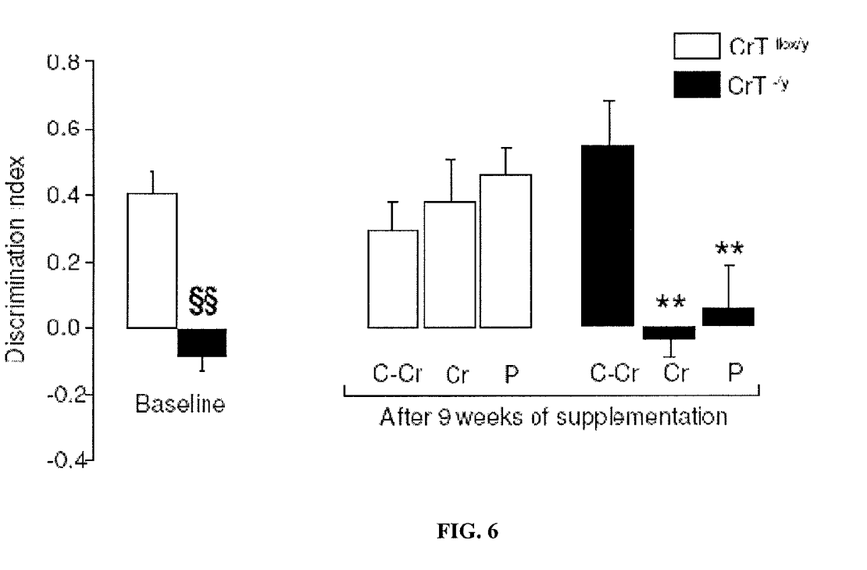
FIG. 6 is a representation of data collected to compare aspects of novel object recognition in mice and the effects of supplementation.
Figure 7:
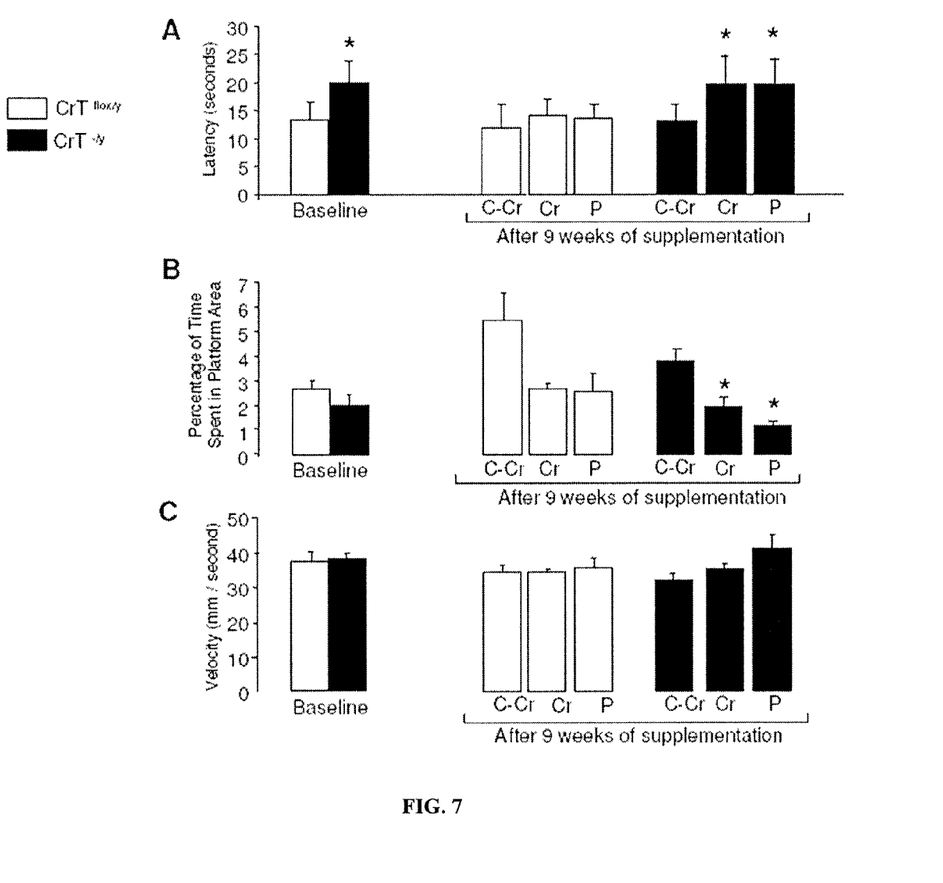
FIG. 7 is a representation of data collected to compare spatial recognition and memory in control versus CRT KO mice and the effects of supplementation.

More specifically, FIGS. 3, 4, 5, and 6 (and Table A) are provided to show, respectively, the following: FIG. 3 uses PCR and actin controls to demonstrate SLC6A8 creatine transporter gene expression in controls versus knockout mice; Table A shows that creatine levels in the brains of the CRT KO mice are substantially lower as compared to controls; FIG. 4A shows that mice treated with cyclocreatine supplementation have higher levels of cyclocreatine in the brains versus placebo treated CRT KO mice; FIG. 5A shows that in CRT KO mice versus controls, the KO mice show lower levels of visible phosphocreatine, and that (FIG. 5B) once the CRT KOs are treated with cyclocreatine, the levels of phosphocreatine in the brains of treated KO mice are greater than the placebo treated group indicating that cyclocreatine is being phosphorylated in the brain successfully; FIG. 6 shows that mice treated with cyclocreatine have better novel object recognition than placebo treated CRT KO mice; and FIG. 7A shows that mice treated with cyclocreatine have a shorter latency in finding hidden platforms than placebo treated CRT KO mice (FIG. 7 shows testing for spatial learning and memory).

Regarding FIG. 3, CRT brain-specific knockout male mice (CRT' or CRT KO mice) and their control littermates (CrTf1"5") were generated by the methods known in the art (e.g., by using the Cre-lox system and homologous recombination as described in Sauer B., Methods, 1998, 14, 381-392; the strategy for targeting the gene deletion to the brain region was based on the data described in Casanova E. et al., Genesis 2001, 31, 37-42). The data shown in FIG. 3 demonstrates absence of the creatine transporter SLC6A8 gene in the brains of the CRT KO mice (marked as $C_R T^{/y}$) and its presence in the brains of control littermates (marked as $CrT^{flox/y}$), as measured by RT-PCR with (β-actin serving as internal control. Cyclocreatine supplementation study was carried out using the CRT KO mice and their control littermates and involved the following measurements before and after cyclocreatine supplementation: a) levels of cyclocreatine in the brain, b) levels of phosphorylated metabolites (e.g. creatine phosphate and cyclocreatine phosphate) in the brain, c) assessment of object recognition memory, and d) assessment of spatial learning and memory. A total 29 CRT KO male mice ($CRT^{/y}$) and 28 control male mice ($CRT^{flox/y}$) at 12 months of age were used in the cyclocreatine supplementation study. The mice were randomly assigned to one of three groups that were started on one of three treatments for 9 weeks: 1) cyclocreatine (C-Cr, CRT KO=7, control=5), 2) creatine (Cr, CRT KO=5, control=5), and 3) maltodextrine as placebo (P, CRT KO=5, control=5). Each treatment drug was supplied in the drinking water and the concentration was adjusted to 0.286 mg/g body weight/day, corresponding to the standard dose of creatine for human subjects (20 g/70 kg body weight/day).

Levels of cyclocreatine and creatine in the organs of CRT KO mice and their control littermates before cyclocreatine supplementation were measured by the methods known in the art (e.g., creatine content was measured as described in Conn R., *Clin. Chem.*, 1960, 6, 537-548; and cyclocreatine content was measured as described in Griffith G. R., *J Biol. Chem.* 1976, 251(7), 2049-2054). Shown in the Table below is creatine content in various organs of the CRT KO mice ($CRT^{/y}$, n=9) and their control littermates ($CRT^{flox/y}$, n=10). The results in the Table indicate that creatine levels in the brains of the CRT KO mice are substantially lower compared to controls (2.8+0.11 versus 11.2±0.74 mmoles/kg ww, P<0.0001). There are no differences in the creatine content between the CRT KO and control mice for all other tissues with the exception of urine, indicative of higher creatine excretion by the CRT KO mice.

The levels of cyclocreatine in the brains of CRT KO mice increased after 9 weeks of cyclocreatine supplementation, as evidenced by the results shown in FIG. 4 (A and B) below. Shown are the levels of A) cyclocreatine and B) creatine in the brain of CRT KO mice. Data is expressed as mean±SE. §P≤0.0001, §§P<0.00001.

The levels of phosphorylated metabolites in the brains of the CRT KO and their control littermates were measured by in vivo magnetic resonance spectroscopy using the procedures well known in the art. The results of these measurements are shown in FIG. 5. Specifically, shown are: A) ratio of peak height in each parameter at baseline and B) ratio of peak height of phospholylated creatine/cyclocreatine after 9 weeks of cyclocreatine supplementation. Data is expressed as mean±SE,*P≤0.05, **P≤0.01. PE=phosphoethanolamine; PC=phosphocholine; GPE=glycerophosphoethanolamine; GPC=glycerophosphocholine; Pi=inorganic phosphate; PCr=phosphocreatine; (β-ATP=β-adenosine triphosphate. FIG. 5A shows lack of phosphocreatine peak and no detectible inorganic phosphate in the CRT KO mice as compared to controls. After treatment with cyclocreatine, a substantial peak co-resonant with the peak position for cyclocreatine phosphate and/or creatine phosphate appears in the CRT KO mice, as shown in FIG. 5B. This indicates that cyclocreatine supplementation increases the levels of cyclocreatine and/or creatine phosphate in CRT KO mice.

Short-term memory of CRT KO mice and their control littermates before and after 9-week cyclocreatine supplementation was measured using the Novel Object Recognition test that is routinely used in the art for evaluation of cognition in rodent models of the disorders of the central nervous system. The results of the Novel Object Recognition test before and after cyclocreatine supplementation is numerically expressed in terms of discrimination indices and is shown in FIG. 6. The results demonstrate that in the absence of cyclocreatine supplementation the CRT KO mice are characterized by a significant impairment in the short-term memory. Cyclocreatine supplementation normalizes the short-term memory in the CRT KO mice. CRT KO mice treated with creatine or placebo (maltodextran) demonstrate no significant changes in their discrimination indexes after treatment at these experimental conditions.

Spatial learning and memory in the CRT KO mice and their control littermates before and after 9-week cyclocreatine supplementation was measured by the Morris Water Maze test, a procedure routinely used in behavioral neuroscience to study spatial learning and memory. During this test, a mouse is placed into a small pool of water containing an escape platform hidden a few millimeters below the water surface. Visual cues are placed around the pool in plain sight of the animal. The mouse swims around the pool in search of an exit while various parameters are recorded, e.g., the time spent in each quadrant of the pool and the time taken to reach the platform (latency). The escape of the mouse from the water reinforces its desire to quickly find the platform, and on subsequent trials (with the platform in the same position) the mouse is able to locate the platform more rapidly. This improvement in performance occurs because the mouse has learned where the hidden platform is located relative to the conspicuous visual cues.

Shown in FIG. 7 (A-C) are the results of the Morris Water Maze test for CRT KO mice and their control littermates before and after cyclocreatine supplementation. Specifically, shown are A) latency to hidden platform in trials, B) percentage of time spent in platform area in probe trial, and C) velocity of swimming in platform area in probe trial. Data is expressed as mean±SE, *P≤0.05. The results demonstrate that cyclocreatine supplementation improves spatial learning and memory in the CRT KO mice.

Those skilled in the art will recognize, or be able to ascertain using no more than routine experimentation, many equivalents to the specific embodiments of the invention described herein. Such equivalents are intended to be encompassed by the following claims.

The entire contents of all references, patents, and patent applications cited herein are expressly incorporated by reference.

The invention claimed is:

1. A method for treating cognitive dysfunction in a subject having a creatine deficiency in the brain due to creatine transporter dysfunction, the method comprising administering to said subject an effective amount of cyclocreatine or a pharmaceutically acceptable salt thereof.

2. The method according to claim 1, wherein the method is a method of treating at least one symptom of cognitive dysfunction in the subject.

3. The method according to claim 2, wherein the subject suffers from creatine transporter deficiency or an inborn error of creatine synthesis.

4. The method according to claim 3, wherein the creatine transporter deficiency is X-linked creatine transporter deficiency.

5. The method according to claim 2, wherein said subject is a human.

6. The method according to claim 2, wherein the subject has a low concentration of creatine in the brain prior to the administration.

7. The method according to claim 2, wherein the at least one symptom comprises a short term memory dysfunction.

8. The method according to claim 2, wherein the at least one symptom comprises a spatial learning dysfunction.

9. The method according to claim 2, wherein the cyclocreatine or pharmaceutically acceptable salt thereof is administered to the subject in combination with a pharmaceutically acceptable carrier.

10. The method according to claim 2, wherein the cyclocreatine or pharmaceutically acceptable salt thereof is administered to the subject orally.

11. The method according to claim 2, wherein the cyclocreatine or a pharmaceutically acceptable salt thereof is formulated as a tablet, powder, solution or suspension.

12. The method according to claim 4, wherein the subject is a heterozygous female carrier of X-linked creatine transporter deficiency.

13. The method according to claim 4, wherein the subject is a male with X-linked creatine transporter deficiency.

* * * * *

SEQUENCE LISTING

```
<160> NUMBER OF SEQ ID NOS: 1

<210> SEQ ID NO 1
<211> LENGTH: 11
<212> TYPE: PRT
<213> ORGANISM: artificial
<220> FEATURE:
<223> OTHER INFORMATION: artificial chemically synthesized

<400> SEQUENCE: 1

Tyr Ala Arg Ala Ala Ala Arg Gln Ala Arg Ala
1               5                   10
```